US00RE50978E

(19) United States
(12) Reissued Patent
Andreevich Suprunov et al.

(10) Patent Number: US RE50,978 E
(45) Date of Reissued Patent: Aug. 4, 2026

(54) INTEGRATED STABILIZER IN DEISOBUTANIZER FOR ISOMERIZATION OF HYDROCARBONS AND PRODUCT SEPARATION

(71) Applicant: Kellogg Brown & Root LLC, Houston, TX (US)

(72) Inventors: Mikhail Andreevich Suprunov, Saint-Petersburg (RU); Oleg Valerievich Gliazov, Saint-Petersburg (RU); Dmitry Nikolaevich Shalupkin, Saint-Petersburg (RU); Andrei Aleksandrovich Kamanovskii, Saint-Petersburg (RU); Nikolai Vladimirovich Litvinenko, Saint-Petersburg (RU); Sergey Yurievich Devyatkov, Saint-Petersburg (RU)

(73) Assignee: Kellogg Brown & Root LLC, Houston, TX (US)

(21) Appl. No.: 18/630,788

(22) Filed: Apr. 9, 2024

Related U.S. Patent Documents

Reissue of:
(64) Patent No.: 11,306,047
Issued: Apr. 19, 2022
Appl. No.: 17/229,527
Filed: Apr. 13, 2021

U.S. Applications:
(60) Provisional application No. 63/011,058, filed on Apr. 16, 2020.

(51) Int. Cl.
*C07C 7/20* (2006.01)
*B01D 3/00* (2006.01)
(Continued)

(52) U.S. Cl.
CPC ..... *C07C 7/20* (2013.01); *B01D 3/009* (2013.01); *B01D 3/322* (2013.01); *B01J 19/245* (2013.01);
(Continued)

(58) Field of Classification Search
CPC ..... C07C 7/20; C07C 5/2702; C07C 7/005; C07C 7/05; B01D 3/009; B01D 3/322; B01J 19/245; B01J 2219/0004
See application file for complete search history.

(56) References Cited

U.S. PATENT DOCUMENTS 6,248,931 B1 6/2001 Davis et al.
11,306,047 B2 4/2022 Suprunov et al.
(Continued)

FOREIGN PATENT DOCUMENTS

CN 1109093 A 9/1995
CN 1763156 A 4/2006
(Continued)

OTHER PUBLICATIONS

"Alkar and Butamer—Two from UOP," C&EN, Apr. 7, 1958, pp. 54-57. (Year: 1958).*
(Continued)

*Primary Examiner* — Alan D Diamond
(74) *Attorney, Agent, or Firm* — Gary M. Machetta

(57) ABSTRACT

An isomerization method consists of a deisobutanizer column receives feed comprising n-butane. The deisobutanizer column delivers its bottoms a portion to a reboiler and another portion along with hydrogen is routed to a isomerization reactor and the reactor effluent is returned to the column. A stabilizer which is integrated with the column, an overhead stream used as a reflux and bottoms containing an iso-butane-rich stream that is the iso-butane product stream. The column overhead effluent is routed to separator, which splits the hydrocarbons and effluent, where the hydrocarbons are routed to deisobutanizer column and effluent recycled to stabilizer, where the stabilizer separates the reactor effluent
(Continued)

Typical scheme of IC4 unit with stabilizer section into product streams contains an iso-butane product stream, a n-butane product stream, and a lighter hydrocarbon product stream.

15 Claims, 3 Drawing Sheets

(51) Int. Cl.

| | |
|---|---|
| ***B01D 3/32*** | (2006.01) |
| ***B01J 19/24*** | (2006.01) |
| ***C07C 5/27*** | (2006.01) |
| ***C07C 7/00*** | (2006.01) |
| ***C07C 7/05*** | (2006.01) |

(52) U.S. Cl.
CPC ..... *C07C 5/2702* (2013.01); *C07C 7/005* (2013.01); *C07C 7/05* (2013.01); *B01J 2219/0004* (2013.01)

(56) References Cited

U.S. PATENT DOCUMENTS

| | | | | |
|---|---|---|---|---|
| 11,697,105 | B2 * | 7/2023 | Suprunov | B01J 23/42 502/159 |
| 2006/0049082 | A1 | 3/2006 | Niccum et al. | |
| 2009/0069617 | A1 * | 3/2009 | Shecterle | C07C 7/144 585/738 |
| 2016/0060191 | A1 * | 3/2016 | Kumar | C07C 9/15 585/737 |
| 2019/0083898 | A1 | 3/2019 | Bhargava et al. | |
| 2019/0329151 | A1 | 10/2019 | Bhargava et al. | |
| 2020/0002248 | A1 | 1/2020 | Krupa et al. | |
| 2020/0109096 | A1 | 4/2020 | DiGiulio et al. | |
| 2021/0277316 | A1 * | 9/2021 | Funk | C10G 61/06 |

FOREIGN PATENT DOCUMENTS

| | | | |
|---|---|---|---|
| CN | 101367720 | A | 2/2009 |
| CN | 104926587 | A | 9/2015 |
| CN | 105154132 | A | 12/2015 |
| CN | 105820838 | A | 8/2016 |
| CN | 106661459 | A | 5/2017 |
| CN | 106661460 | A | 5/2017 |
| CN | 107304152 | A | 10/2017 |
| CN | 110790627 | | 2/2020 |
| CN | 115397553 | A | 11/2022 |
| GB | 2609807 | | 2/2023 |
| IN | 202217064129 | B | 10/2023 |
| WO | 2015047682 | A1 | 4/2015 |
| WO | 2019060324 | A2 | 3/2019 |
| WO | 2021211604 | | 10/2021 |

OTHER PUBLICATIONS

International Searching Authority, Patent Cooperation Treaty; PCT International Search Report and Written Opinion dated Jul. 7, 2021 for International Application No. PCT/US 2021/027112 filed Apr. 13, 2021 (14 pages).

Chinese National Intellectual Property Administration, First Office Action dated Dec. 21, 2023 for Chinese Application No. CN2021800278602 (10 pages).

The Controller of Patents, the Patent Office Delhi; First Examination Report for Indian Patent Application No. 202217064129 filed Oct. 11, 2022; 5 pages.

European Patent Office; European Search Report dated Apr. 12, 2024 for European Patent No. 21788392.5 filed Nov. 11, 2022; 6 pages.

Edward Griffiths; Gulf Downstream Association; International Downstream Conference & Exhibition; New Innovative Approach to Increase Isomerization throughput and Octane Booster; Oct. 2018; 17 pages.

* cited by examiner

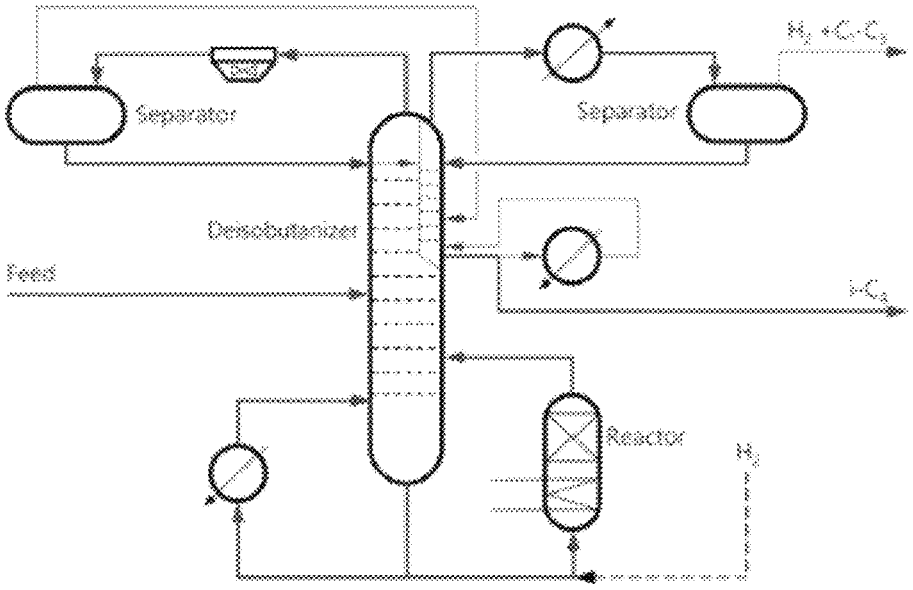
Figure 1 – Typical scheme of IC4 unit with stabilizer section

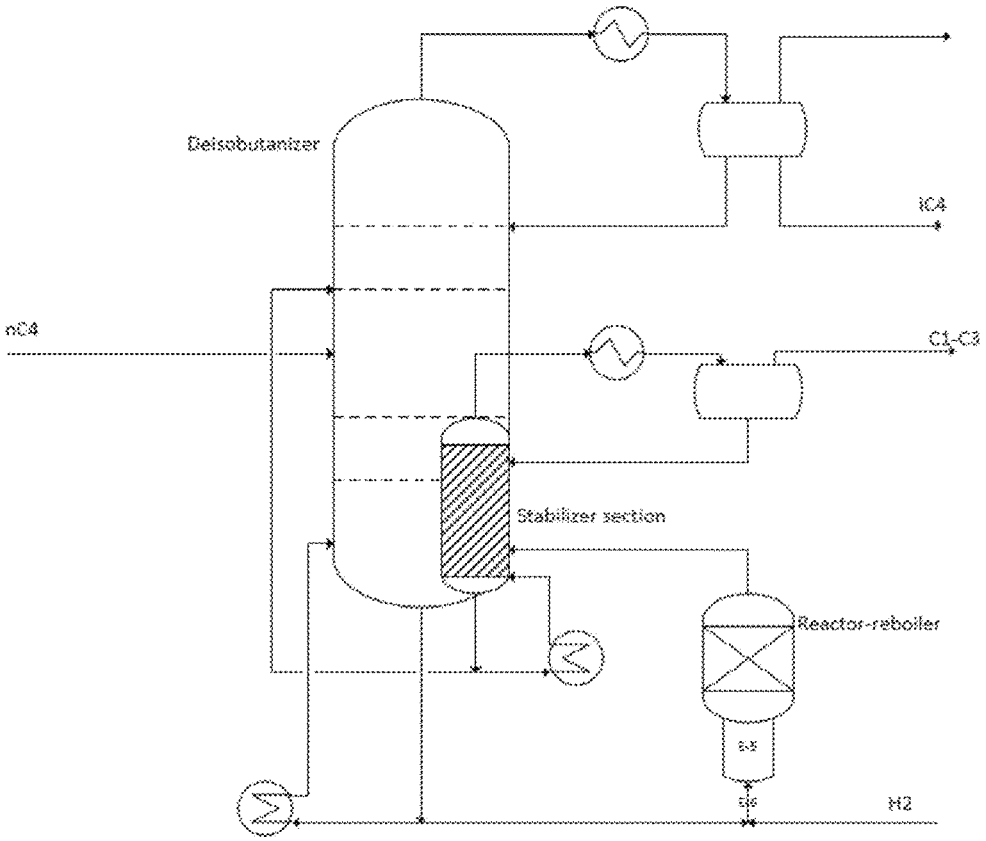
Figure 2 – Stabilizer section in the bottom of the deisobutanizer

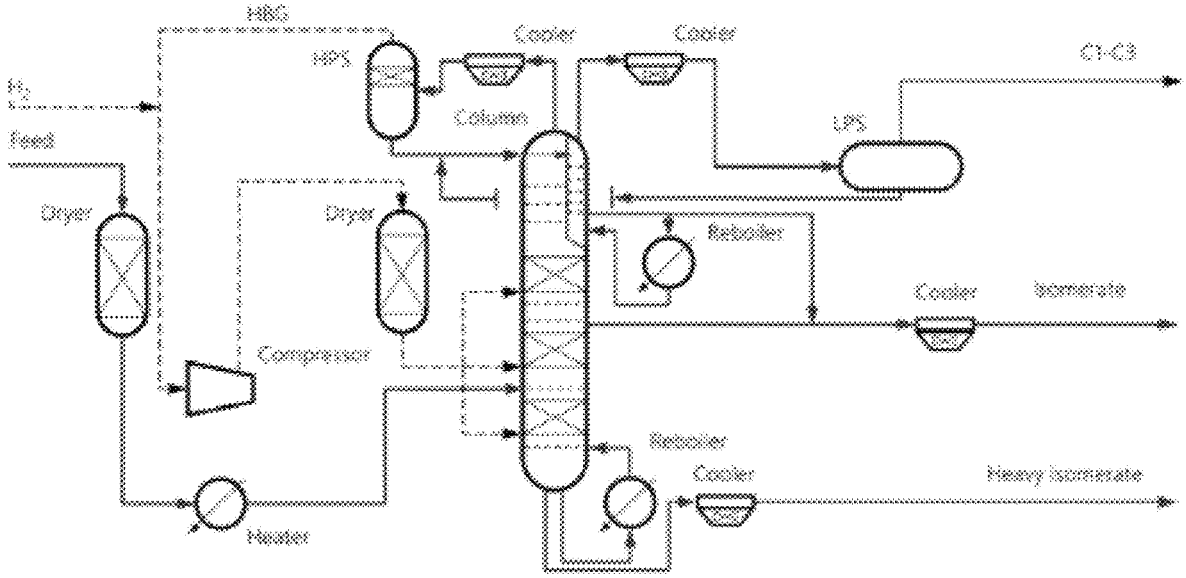
Figure 3 – Typical scheme of MAX-ISOM unit with stabilizer section

INTEGRATED STABILIZER IN DEISOBUTANIZER FOR ISOMERIZATION OF HYDROCARBONS AND PRODUCT SEPARATION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

[This application] *This application is an application for reissue of U.S. Pat. No. 11,306,047, issued on Apr. 19, 2022, entitled "Integrated Stabilizer in Deisobutanizer for Isomerization of Hydrocarbons and Product Separation" and filed on Apr. 13, 2021, as U.S. patent application Ser. No. 17/229,527, which* claims priority to U.S. Provisional Patent Application having Ser. No. 63/011,058 filed on Apr. 16, 2020 which is incorporated by reference herein.

TECHNICAL FIELD

The present invention relates to isomerization of hydrocarbons and fractionation of the product effluent stream for effective separation of iso-paraffins from feedstock and more particularly relates to such isomerization processes that include an integrated stabilizer in fractionation section.

BACKGROUND

About 90% of the total butane consumption in the United States is in gasoline manufacture where n-butane is used directly as a blending component, and isobutane is either used for the production of high octane alkylate or for the production of isobutylene to make methyl tert-butyl ether. Chemical uses account for another 6-8% of the total butanes. Due to the recent increased demand for high octane gasoline and the federally regulated reduction of gasoline vapor pressure, there is the need to have a process that can effectively convert normal butane to isobutane to ultimately increase the production of high octane blending components.

As the boiling points of normal butane and isobutane are relatively close and a relatively pure isobutane product is desired, the deisobutanizer typically is operated with a high reflux ratio. Thus, the heat duty of the deisobutanizer is a significant component of the operating costs of a butane isomerization process, and the heat duty becomes increasingly significant as higher purity isobutane product streams are sought. Accordingly, improved normal butane isomerization processes are sought that have improved capital and operating cost.

The objective of the present invention is Methods and apparatuses for the isomerization of hydrocarbons and fractionation having reduced reflux demand and reboiler duty by Stabilizer integrated with deisobutanizer columns.

SUMMARY

An isomerization system consists of a deisobutanizer column receives feed comprising n-butane. The deisobutanizer column delivers its bottoms a portion to a reboiler and another portion along with hydrogen is routed to an isomerization reactor and the reactor effluent is returned to the column. A stabilizer which is integrated with the column, an overhead stream of stabilizer used as a reflux and bottoms containing an iso-butane-rich stream that is iso-butane product stream.

BRIEF DESCRIPTION OF THE DRAWINGS

FIG. 1—Typical scheme of iso-butane unit with stabilizer section; isomerization of n-butane to iso-butane by stabilizer integrated with deisobutanizer column;

FIG. 2—Stabilizer section in the bottom of the deisobutanizer; isomerization of n-butane to iso-butane by stabilizer integrated at the bottom of the deisobutanizer column;

FIG. 3—Typical scheme of isomerization unit with stabilizer section; isomerization of hydrocarbons i.e. n-butane, n-pentane, n-hexane, n-heptane, to isomerate and heavy isomerate by stabilizer integrated with Catalytic distillation column;

DETAILED DESCRIPTION

An isomerization system consists of a deisobutanizer column receives feed comprising n-butane. The deisobutanizer column delivers its bottoms a portion to a reboiler and another portion along with hydrogen is routed to an isomerization reactor and the reactor effluent is returned to the column. A stabilizer which is integrated with the column, an overhead stream of stabilizer used as a reflux and bottoms containing an iso-butane-rich stream that is the iso-butane product stream.

Methods and apparatuses for the isomerization of hydrocarbons and fractionation of the product effluent stream. Stabilizer columns have been traditionally used in isomerization of hydrocarbons. The invention could provide an isomerization process having lower capital costs and lower utilities costs due to the integration of the stabilizer section into the rectification or reaction-rectification column. The reduction of reflux demand of the distillation column due to the heat exchange between stabilizer and distillation sections, the reduction of reboiler duty are the effects of the invention. Exemplary embodiments are provided below.

More specifically as shown in FIG. 1, n-C4 isomerization; stabilizer section integrated into the top of the deisobutanizer. One exemplary embodiment can be a process for isomerizing a feed stream including n-butane. The feed stream comprising of n-butane is sent to the deisobutanizer column. The deisobutanizer column delivers its bottoms a portion to a reboiler and another portion from its bottom or from a tray located above the bottom along after mixing with hydrogen is routed to a isomerization reactor and the reactor effluent is returned to the column . . . . The overhead stream of the deisobutanizer is partially used as reflux and partially sent to the stabilization section, which is integrated into the top of the deisobutanizer column. C1-C3 hydrocarbons are removed in the section and the bottom product contains at least 93% wt of isobutane. compared to traditional schemes, in which the reactor effluent is sent to the stabilizer column first, present scheme has lowered specific overall reflux demand and reboiler duty.

Another embodiment of the invention as shown in FIG. 2, n-C4 isomerization; stabilizer section integrated into the bottom of the deisobutanizer. Another exemplary embodiment can be a process for n-butane isomerizing. The stabilizer section is integrated into the bottom part of the deisobutanizer column. The feed stream comprising of n-butane is sent to the deisobutanizer column. The deisobutanizer column delivers its bottoms a portion to a reboiler and another portion from its bottom or from a tray located above the bottom after mixing with hydrogen is routed to a isomerization reactor. The output stream of the reactor is sent to the stabilizer section, where C1-C3 hydrocarbons are removed. The bottom stream of the stabilizer section is partially reboiled and partially sent to the deisobutanizer column. Commercial iC4 product is taken from the overhead stream of the deisobutanizer. heat integration between stabilizer section and bottom part of deisobutanizer column allows to lower the reboiler duty on the deisobutanizer column.

Another embodiment of the invention as shown in FIG. 3, Isomerization technology with integrated stabilizer section. Another exemplary embodiment is a process for isomerizing a C5-C6 and/or C6-C7 fractions. The process includes providing a hydrocarbon stream to the reaction-rectification column. The top product from the high pressure separator is returned into the column as reflux, another part is sent to the stabilization section integrated into the top of the reaction-rectification column. C1-C3 hydrocarbons are removed in the section, the bottom product which contains mostly branched C5+ hydrocarbons is admixed with isomerate product out of the column. Present invention provides lowered reflux demand due to the heat integration of stabilizer section and distillation part of the column.

A catalytic distillation column receives feed, wherein some part of the feed goes down through the catalytic distillation column to a reboiler and leaves the column as heavy isomerate. Light fraction of the feed goes upward through the catalytic distillation column. A stabilizer which is integrated with the column, an overhead stream used as a reflux after separating the lighter hydrocarbons through low pressure separator and bottoms of stabilizer containing an isomerate rich product stream, a portion is recycled to stabilizer after reboil through reboiler. the column overhead effluent is routed to high pressure separator, which splits the hydrocarbons and effluent hydrogen, where the hydrocarbons are routed to stabilizer in the column, which is integrated with top of the catalytic distillation column and effluent hydrogen recycled to column through compressor and dryer. The column has a side-draw product that is isomerate. The isomerate-rich stream is taken from a point selected from the side draw of an catalytic distillation column and or a bottom section of the stabilizer. The side draw isomerate-rich stream is vapor, liquid, or a combination thereof.

The stabilizer comprises an overhead cooler configured to condense vapors from the column and the stabilizer. A reflux stream from the overhead condenser is fed to a top tray of the stabilizer.

It will be appreciated that the system and process described herein are not limited to any particular temperature ranges, pressure ranges, flow rates, stream compositions, and the like. It is expected that the system and process, now that it is described, can be modified by one of ordinary skill in the art to be applicable to a variety of reactor effluent compositions and other conditions and parameters as necessary.

It will also be appreciated that the systems and processes described herein will have a number of technical and commercial advantages. Technical advantages include, but are not necessarily limited to:

Improvement of fractionation efficiency;

Reduced utility requirements;

Reduced overall energy requirements;

Reduced reflux demand;

Reduced reboiler duty; and

Reduced iso-butane loss from the system.

Commercial advantages include, but are not necessarily limited to:

20-30% less capital requirement as compared to the conventional column solutions;

Improvement in fractionation economics;

Less plot space (equipment footprint) requirement;

Advantages for plant upgrading/debottlenecking;

Overall improvement in the value of products; and

Alternative use of existing assets to improve overall economics of the plant.

In the foregoing specification, the invention has been described with reference to specific embodiments thereof. However, the specification is to be regarded in an illustrative rather than a restrictive sense. For example, equipment, columns, stabilizer, processes, reactants, n-paraffins, isoparaffins, products, isomerate, and operating conditions falling within the claimed or disclosed parameters, but not specifically identified or tried in a particular example, are expected to be within the scope of this invention.

The present invention may be practiced in the absence of an element not disclosed. In addition, the present invention may suitably comprise, consist or consist essentially of the elements disclosed. An isomerization system consists of a deisobutanizer column or catalytic distillation column receives feed comprising n-butane. The deisobutanizer column delivers its bottoms a portion to a reboiler and another portion along with hydrogen is routed to an isomerization reactor and the reactor effluent is returned to the column. A stabilizer which is integrated with the column, an overhead stream of stabilizer used as a reflux, lighter hydrocarbons i.e. C1-C3 hydrocarbons and bottoms containing an iso-butane-rich stream that is the iso-butane product stream.

The words "comprising" and "comprises" as used throughout the claims, are to be interpreted to mean "including but not limited to" and "includes but not limited to", respectively.

As used herein, the word "substantially" shall mean "being largely but not wholly that which is specified."

As used herein, the singular forms "a," "an," and "the" are intended to include the plural forms as well, unless the context clearly indicates otherwise.

As used herein, the term "about" in reference to a given parameter is inclusive of the stated value and has the meaning dictated by the context (e.g., it includes the degree of error associated with measurement of the given parameter).

As used herein, the term "and/or" includes any and all combinations of one or more of the associated listed items.

The invention claimed is:

1. An isomerization [n-paraffins] *and fractionation system* comprising:

a deisobutanizer column [receives] *comprising a* feed comprising n-paraffins, [containing feedstock, it delivers] *a bottoms stream, and a deisobutanizer column overhead stream;*

[a portion to] a reboiler *arranged to receive at least a first portion of the bottoms stream from the deisobutanizer column*;

an isomerization reactor [receives another] *arranged to receive a second* portion *of the bottoms stream* from *the* deisobutanizer column [bottom] or *an effluent* from a tray located above *an output of* the [bottom after mixing] *bottoms stream in the deisobutanizer column, and configured to mix the second portion of the bottoms stream or the effluent from the tray located above the*

*output of the bottoms stream* with hydrogen [and] *to yield a reactor effluent, wherein* the reactor effluent is [returned] *directed* to the *deisobutanizer* column;

a stabilizer [which is] integrated with the *deisobutanizer* column, [an] *the stabilizer comprising a stabilizer* overhead stream [used] *provided* as a reflux *to the stabilizer* and *a stabilizer* bottoms containing an isomerate rich stream that is *an* isomerate product stream; *and* a separator [which receives] *arranged to receive* the *deisobutanizer* column overhead stream, [which splits the] *the separator configured to split* hydrocarbons *in the deisobutanizer column overheard stream* into at least two *overhead* streams, wherein [the first] *at least one overhead* stream is routed to *the* deisobutanizer column as [its] reflux, and [the rest] *any remaining overhead* streams are routed to the stabilizer[;

where the stabilizer separates the reactor effluent into product streams comprising:

an isomerate product stream, and a lighter hydrocarbon product stream].

2. The [isomerization n-paraffins] *system* of claim 1, where at least a portion of the isomerate product stream is recycled to the stabilizer in a recycle stream.

3. The [isomerization n-paraffins] *system* of claim 1, where the stabilizer [separates] *is configured to separate* the isomerate effluent into branched C4+ hydrocarbons, and *a* lighter hydrocarbon product stream along with hydrogen.

4. The [isomerization n-paraffins] *system* of claim 1, further comprising an intermediate reboiler in a bottom section of the [reboiler] *stabilizer*, [and where] *wherein* the isomerate product stream is a heating medium in the intermediate reboiler.

5. A method for isomerization of n-butane [comprises] *comprising*:

*feeding an* n-butane-rich fraction [is a feed] to [the] *a* deisobutanizer column containing *an integrated* stabilizer;

[a reactor effluent is a feed to a deisobutanizer column containing stabilizer;]

*delivering a first portion of a bottoms stream of* the deisobutanizer column [delivers its bottoms a portion] to a reboiler*;*

[and another] *mixing a second* portion [after mixing with hydrogen is routed] *of the bottoms stream of the deisobutanizer column with hydrogen to form a mixture and delivering the mixture to an isomerization reactor;*

[to an] *routing a reaction effluent from the* isomerization reactor [and the reactor effluent is returned] to the *integrated* stabilizer[;] *in the deisobutanizer column,*

[the stabilizer integrated with column of the deisobutanizer column;]

*wherein,* the stabilizer has an overhead [light hydrocarbons that is] *comprising* C1-C3 hydrocarbons and hydrogen; *and*

*withdrawing from* the *deisobutanizer* column [has] an overhead [product withdrawn from the column and/or stabilizer that is] isomerate [stream that is the] *product comprising an* iso-butane product stream.

6. The method of claim 5, [where] *further comprising recycling a portion of* the [overhead iso-butane-rich] *iso-butane product* stream [is a recycle stream] to the deisobutanizer column.

7. The method of claim 5, further comprising *feeding a bottoms stream from the integrated stabilizer to* an intermediate reboiler [in] *provided at* a bottom section of the deisobutanizer *column*.

8. An isomerization *and fractionation* method [for n-paraffin's] comprising:

[a catalytic distillation column receives feed] *feeding a feed* comprising n-paraffins[,] *to a catalytic distillation column, wherein the catalytic distillation column comprises an integrated stabilizer;*

[which catalytic distillation column delivers its bottoms a portion] *delivering a first portion of a bottoms stream of the catalytic distillation column* to a reboiler, [and another] *wherein a second* portion [is] *of the bottoms stream of the catalytic distillation column comprises* a heavy isomerate;

[a stabilizer which is integrated with the column,] *separating lighter hydrocarbons from* an overhead stream [used as a reflux after separating the lighter hydrocarbons through] *of the integrated stabilizer via a* low pressure separator [and] *to yield a remaining overhead stream of the integrated stabilizer, and using the remaining overhead stream of the integrated stabilizer as reflux to the integrated stabilizer;*

*reboiling using a reboiler and then recycling a portion of the* bottoms *stream* of *the integrated* stabilizer, [containing] *wherein the bottoms stream of the integrated stabilizer comprises* an isomerate rich product stream[, a portion is recycled to stabilizer after reboiling through reboiler];

[the column] *routing an* overhead effluent [is routed] *of the catalytic distillation column* to *a* high pressure separator[, which splits the] *to separate* hydrocarbons and effluent hydrogen, [where] *and directing* the hydrocarbons [are routed] to *the integrated* stabilizer in *a top portion of* the [column, which is integrated with top of the deisobutanizer column] *catalytic distillation column*; *and*

[the column has a side-draw product that is] *withdrawing an* isomerate[;] *product stream from the catalytic distillation column*

[where the stabilizer separates the reactor effluent into product streams comprising:

an isomerate product stream, and a light hydrocarbon stream].

9. The isomerization method of claim 8, where the feed [is] *comprises* C5-C6, C6-C7, *or* C5-C7 fractions.

10. The isomerization method of claim 8, where the lighter [hydrocarbon product stream containing] *hydrocarbons comprise* C1-C3 hydrocarbons.

11. The isomerization method of claim 8, where the isomerate product stream [is] *comprises* branched C4+ hydrocarbons.

12. The isomerization method of claim 8, further comprising *employing the isomerate product stream as a heating medium in* an intermediate reboiler [in] *at* a bottom section of the [reboiler, and where the isomerate product stream is a heating medium in the intermediate reboiler] *integrated stabilizer*.

[13. The isomerization method of claim 8 where the stabilizer at or near the top or near the bottom of the column.]

14. The isomerization method of claim 8, where the [isomerate-rich] *isometric product* stream is [taken] *withdrawn* from a point selected from [the] *a* side draw of the catalytic distillation column and or a bottom section of the stabilizer.

15. The isomerization method of claim [8] *14*, where the side draw [that is isomerate-rich] *isomarate product* stream [is selected from the group consisting of] *comprises* vapor, liquid, or a combination thereof.

16. The isomerization method of claim 8, where the [isomerate-rich] *isomarate product* stream [is a] *comprises* branched C4+ hydrocarbons.

* * * * *